(12) United States Patent
Wilson et al.

(10) Patent No.: US 8,133,256 B2
(45) Date of Patent: Mar. 13, 2012

(54) SHAPE MEMORY POLYMER FOAMS FOR ENDOVASCULAR THERAPIES

(75) Inventors: Thomas S. Wilson, Castro Valley, CA (US); Duncan J. Maitland, Pleasant Hill, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 2436 days.

(21) Appl. No.: 10/801,355

(22) Filed: Mar. 15, 2004

(65) Prior Publication Data

US 2005/0075405 A1 Apr. 7, 2005

(51) Int. Cl.
*A61B 17/03* (2006.01)

(52) U.S. Cl. ........................................................ 606/213

(58) Field of Classification Search .................. 606/108, 606/213–217
See application file for complete search history.

(56) References Cited

U.S. PATENT DOCUMENTS

| | | | |
|---|---|---|---|
| 5,192,301 A * | 3/1993 | Kamiya et al. ................. 606/213 |
| 5,207,709 A * | 5/1993 | Picha ........................... 623/23.74 |
| 5,330,483 A | 7/1994 | Heaven et al. |
| 5,429,583 A | 7/1995 | Paulus et al. |
| 5,634,936 A * | 6/1997 | Linden et al. ................. 606/213 |
| 5,674,242 A | 10/1997 | Phan et al. |
| 5,762,630 A | 6/1998 | Bley et al. |
| 5,895,398 A | 4/1999 | Wensel et al. |
| 5,911,737 A | 6/1999 | Lee et al. |
| 5,957,966 A | 9/1999 | Schroeppel et al. |
| 5,964,744 A | 10/1999 | Balbierz et al. |
| 6,034,149 A * | 3/2000 | Bleys et al. ................... 521/155 |
| 6,059,815 A | 5/2000 | Lee et al. |
| 6,090,072 A | 7/2000 | Kratoska et al. |
| 6,102,917 A | 8/2000 | Maitland et al. |
| 6,599,234 B1 | 7/2003 | Gray et al. |
| 2002/0095169 A1* | 7/2002 | Maitland et al. .............. 606/194 |
| 2002/0113066 A1 | 8/2002 | Stark et al. |
| 2002/0165582 A1* | 11/2002 | Porter ........................... 606/213 |
| 2005/0182428 A1* | 8/2005 | Bearinger et al. ............ 606/151 |

OTHER PUBLICATIONS

Cetas, T.C., et al., "A Ferrite Core/Metallic Sheath Thermoseed for Interstitial Thermal Therapies," IEEE Transactions on Biomedical Engineering, vol. 45, No. 1, Jan. 1998, pp. 68-77.

Oleson, James R., "A Review of Magnetic Induction Methods for Hyperthermia Treatment of Cancer," IEEE Transactions on Biomedical Engineering, vol. BME-31, No. 1, Jan. 1984, pp. 91-97.

Sato, M., et al., "An Experimental Study on a Soft Heating Method for Clinical Application of Interstitial Hyperthermia," IEEE Transactions on Magnetics, vol. 29, No. 6, Nov. 1993, pp. 3331-3333.

Jojo, M., et al., "Consideration of Handy Excitation Apparatus for the Inductive Hyperthermia," IEEE Transactions on Magnetics, vol. 37, No. 4, Jul. 2001, pp. 2944-2946.

Paulus, J.A., et al., "Evaluation of Inductively Heated Ferromagnetic Alloy Implants for Thereapeutic Interstitial Hyperthermia," IEEE Transactions on Biomedical Engineering, vol. 43, No. 4, Apr. 1996, pp. 406-413.

(Continued)

*Primary Examiner* — Kathleen Sonnett
(74) *Attorney, Agent, or Firm* — Eddie E. Scott

(57) ABSTRACT

A system for occluding a physical anomaly. One embodiment comprises a shape memory material body wherein the shape memory material body fits within the physical anomaly occluding the physical anomaly. The shape memory material body has a primary shape for occluding the physical anomaly and a secondary shape for being positioned in the physical anomaly.

24 Claims, 5 Drawing Sheets

OTHER PUBLICATIONS

Wetzel, E., et al., "Feasibility of Magnetic Particle Films for Curie Temperature-Controlled Processing of Composite Materials," Army Research Laboratory, ARL-TR-2431, Mar. 2001, 58 pages.

McCurrie, R.A., "Ferromagnetic Materials Structure and Properties," Academic Press, Longon, 1994, 4 pages.

Jordan, J., et al., "Inductive Heating of Ferrimagnetic Particles and Magnetic Fluids: Physical Evaluation of Their Potential for Hyperthermia," Int. J. Hyperthermia, vol. 9, No. 1, 1993, pp. 51-68.

Matsuki, H., et al., "High Quality Soft Heating Method Utilizing Temperature Dependence of Permeability and Core Loss of Low Curie Temperature Ferrite," IEEE Transactions on Magnetics, vol. MAG-21, No. 5, Sep. 1985, pp. 1927-1929.

Stauffer, P. R., "Observations on the Use of Ferromagnetic Implants for Inducing Hyperthermia," IEEE Transactions on Biomedical Engineering, vol. BME-31, No. 1, Jan. 1984, pp. 76-90.

Hergt, R., et al., Physical Limits of Hyperthermia Using Magnetite Fine Particles, IEEE Transactions on Magnetics, vol. 34, No. 5, Sep. 1998, pp. 3745-3754.

Stauffer, P. R., "Practical Induction Heating Coil Designs for Clinical Hyperthermia with Ferromagnetic Implants," IEEE Transactions on Biomedical Engineering, vol. 41, No. 1, Jan. 1994, pp. 17-28.

Irie, M., "Shape Memory Polymers" (Chapter 9) from book "Shape Memory Materials," Cambridge University Press, United Kingdom, 1998, 19 pages.

Atkinson, W. J., et al., "Usable Frequencies in Hyperthermia with Thermal Seeds," IEEE on Biomedical Engineering, vol. BME-31, No. 1, Jan. 1984, pp. 70-75.

Kimura, I., et al., "VLF Induction Heating for Clinical Hyperthermia," IEEE Transactions on Magnetics, vol. MAG-22, No. 6, Nov. 1986, pp. 1897-1900.

* cited by examiner

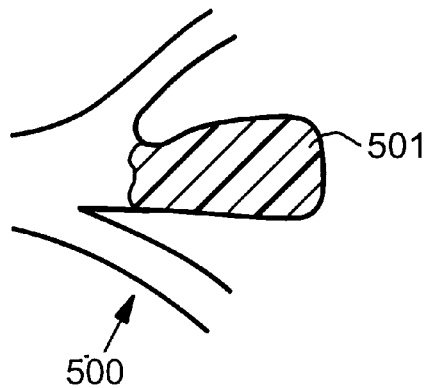
FIG. 5
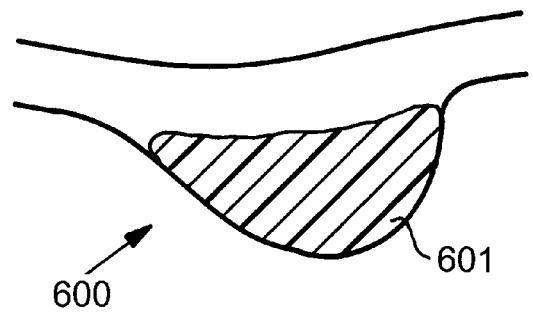
FIG. 6
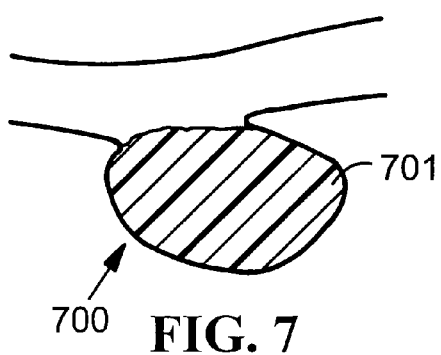
FIG. 7
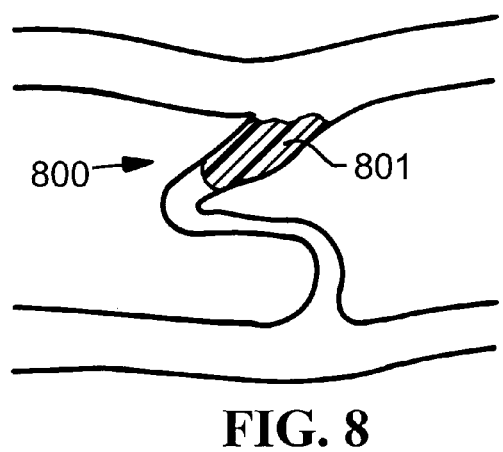
FIG. 8
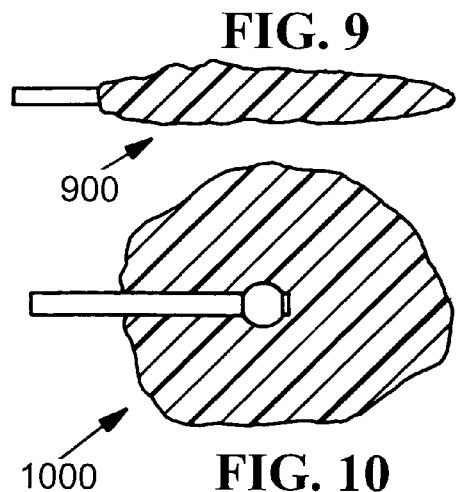
FIG. 9
FIG. 10
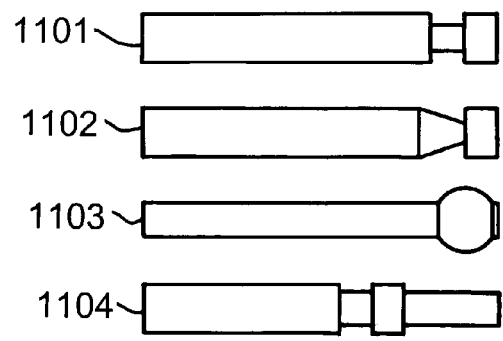
FIG. 11

SHAPE MEMORY POLYMER FOAMS FOR ENDOVASCULAR THERAPIES

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to Endovascular Therapies and more particularly to Shape Memory Polymer Foams for Endovascular Therapies.

2. State of Technology

United States Patent Application 2003/0144695 by James, F. McGuckin and Richard T. Briganti, published Jul. 31, 2003, and United States Patent Application 2003/0009180 by Peter W. J. Hinchliffe, James, F. McGuckin, Richard T. Briganti, and Walter H. Peters, published Jan. 9, 2003, for a vascular hole closure device provides the following state of the technology information, "During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery."

United States Patent Application 2002/0133193 published Sep. 19, 2002, and U.S. Pat. No. 6,391,048 issued May 21, 2002, to Richard S. Ginn and W. Martin Belef, for an integrated vascular device with puncture site closure component and sealant and methods of use provides the following state of the technology information, "Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure. Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis."

U.S. Pat. No. 6,174,322 issued Jan. 16, 2001 to Bernhard Schneidt for an Occlusion device for the closure of a physical anomaly such as a vascular aperture or an aperture in a septum provides the following state of the technology information, "The human circulatory system is comprised of a cardiovascular circulation and pulmonary circulation. In the embryonic phase of the development of a human being, the two circulatory systems are joined by the ductus arteriosus. The ductus connects the aorta (systemic circulation) with the pulmonary artery (pulmonary circulation). In the normal development of an infant, this ductus closes after birth. In pathological development, the ductus may not close so that the two circulatory systems remain connected even after birth. This can reduce the life expectancy of the infant. Closure of the ductus by means of a surgical procedure is well-known. However, this procedure is very cost-intensive and is connected with a risk for the patient. Closure of the ductus by means of an IVALON® (polyvinyl alcohol) foam plug (Porstmann method) is also well-known. In this case, a guide rail is introduced via a femoral vein into the aorta, through the ductus into the pulmonary artery and from there through the right ventricle and the right atrium and finally to the outside again via the opposite femoral vein. The ductus plug is then pushed into the ductus where it is "jammed in place." Owing to the high pressure differential 1 between the aorta and pulmonary artery, high demands are placed on the fixation of the ductus plug within the ductus."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for occluding a physical anomaly. One embodiment of the present invention comprises a shape memory material body wherein the shape memory material body fits within the physical anomaly occluding the physical anomaly. The shape memory material body has a primary shape for occluding the physical anomaly and a secondary shape for being positioned in the physical anomaly. In one embodiment, the shape memory material body comprises a shape memory polymer. In another embodiment, the shape memory material body comprises a shape memory polymer foam.

One embodiment of the present invention comprises a method for occluding a physical anomaly. The method comprises the steps of providing a shape memory material body with a secondary shape for being positioned in the interior of the physical anomaly and a larger primary shape for occluding the anomaly, positioning the shape memory material body in the interior of the physical anomaly when the shape memory material body is in the secondary shape, and causing the closure body to change to the larger primary shape for occluding the anomaly. In one embodiment, the step of providing a shape memory material body with a secondary shape for being positioned in the interior of the physical anomaly and a larger primary shape for occluding the anomaly comprises providing a shape memory polymer foam body with a secondary shape for being positioned in the interior of the physical anomaly and a larger primary shape for occluding the anomaly.

One embodiment of the present invention comprises a system for occluding a physical anomaly. The embodiment comprises a shape memory material body means for occluding the anomaly, the shape memory material body means having a secondary shape for being positioned in the interior of the physical anomaly and a larger primary shape, means for positioning the shape memory material body in the interior of the physical anomaly when the shape memory material body is in the secondary shape, and means for causing the shape memory material body to change to the larger primary shape for occluding the anomaly. In one embodiment, the shape memory material body means comprises a shape memory polymer body with a secondary shape for being positioned in the interior of the physical anomaly and a larger primary shape for occluding the anomaly. In another embodiment, the shape memory material body means comprises a shape memory polymer foam body with a secondary shape for being positioned in the interior of the physical anomaly and a larger primary shape for occluding the anomaly.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 5 illustrates an embodiment of a foam device system.

FIG. 6 illustrates another embodiment of a foam device system.

FIG. 7 illustrates another embodiment of a foam device system.

FIG. 8 illustrates another embodiment of a foam device system.

FIG. 9 shows collapsed SMP foam device.

FIG. 10 shows an expanded SMP foam device.

FIG. 11 shows embodiments of the distal ends of guidewires.

DETAILED DESCRIPTION OF THE INVENTION

Figure 1:
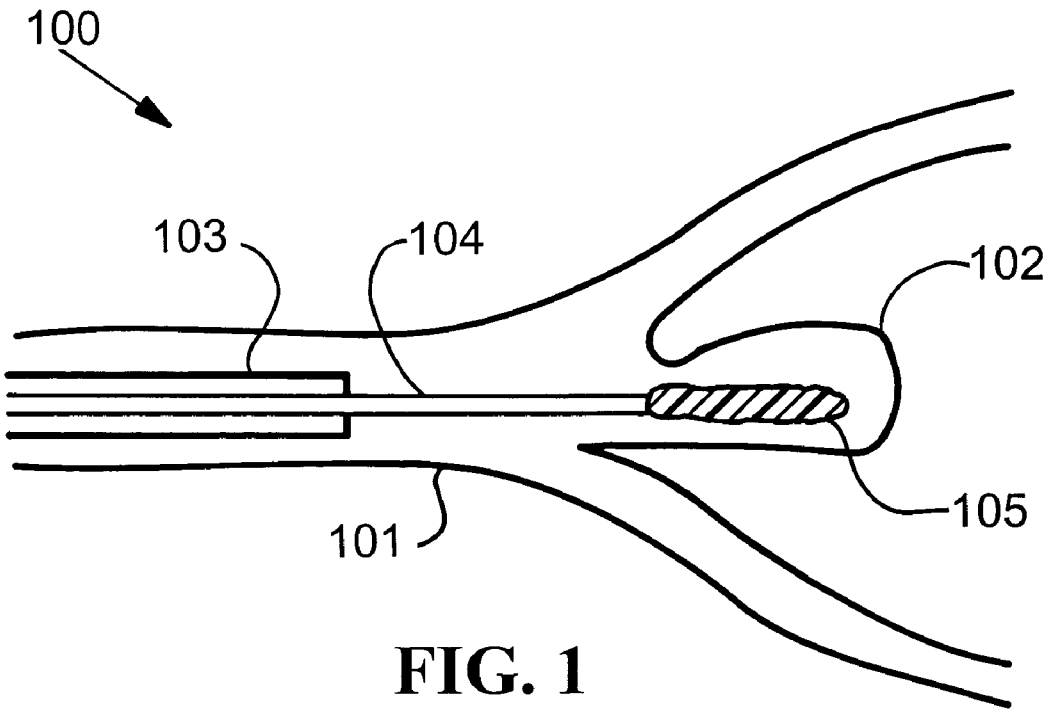
FIG. 1 illustrates an embodiment of the present invention that provides a system for occluding a physical anomaly.

Referring now to the drawings, to the following detailed description, and to incorporated materials, detailed information about the invention is provided including the description of specific embodiments.

The present invention provides a system for occluding a physical anomaly. Various embodiments are contemplated. For example, one embodiment provides a system for treating an arteriovenous malformation. In this embodiment a shape memory device is transferred into the arteriovenous malformation. The shape memory device is actuated expanding it inside the arteriovenous malformation and occluding the arteriovenous malformation.

In the general application, a vascular anomaly is treated using the device with the intent of stabilizing the anomaly from further expansion and possible rupture. The device is delivered endovascularly to the site for therapy via a catheter. The catheter may be previously placed using a conventional guidewire or the device may be installed using the guidewire. Once the catheter is placed near the therapeutic site, the device is placed into the anomaly with the guidewire and guided visually by radiology. The device is then held in place and the foam is actuated to expand, filling the anomaly. Once expanded, the foam will stay in place on its own or an additional aid will be used to hold it in place; for example, a diaphragm for the aneurysm or a stent for the AVM. The foam is released from the guidewire or catheter via the expansion process or following actuation by known techniques. The guidewire and/or catheter is then retracted and the therapy is completed. Should there be a misplacement of the foam, retrieval is possible using another shape-memory polymer device or other conventional techniques.

Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while is an elastomeric state and that shape is fixed in one of several ways including cooling the polymer below a crystalline, liquid crystalline, or glass transition temperature; by inducing additional covalent or ionic crosslinking, etc.

While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower Tg) or physical restraints (physical or chemical crosslinks). Actuation then occurs for the recovery to the primary shape by removing that restraint, e.g., heating the polymer above its glass transition or melting temperature, removing ionic or covalent crosslinks, etc. Other types of polymers which undergo shape memory behavior due to photon induced conformational transformations, conformational changes (e.g., rod-coil transition) due to changes in chemical environment (pH, ionic strength, etc.), or structural changes due to imposed fields (e.g., electric, magnetic, . . . ) may also be used. Both shape memory alloys (SMAs) and shape memory polymers (SMPs) can be used for the shape memory material of the present invention.

A shape memory material therapeutic device has advantages over existing therapeutic devices of being able to be moved more easily through the catheter to the point of placement, A shape memory material therapeutic can be placed more precisely within the geometry of the vascular disorder, and there is a higher degree of control over the expansion process while the device was being held in the desired position. A shape memory material therapeutic can be controllably expanded while being held in precise placement. A shape memory material therapeutic expands to its secondary shape within a few seconds, which is much faster than current expandable hydrogel based devices. The modulus of the devices can be accurately controlled so that expansion forces are low and no damage is done to areas of the vascular lumen.

The shape memory material device is expandable from 100% to 10000% by volume. The shape memory material device is actuated by one of several means including electromagnetic energy delivered optically. The shape memory material device is used to occlude part or all of a lumen, aneurysm, artiovascular malformation, or other physical anomaly.

The present invention also provides a process for making SMP foams with specific pore structures; geometric shaping of the SMP device to fit specific physiological geometries; the coating of the surface of the SMP to enhance biocompatibility and promote integration into the body; the development of a complete therapeutic device for aneurysm (and AVM) treatment which includes techniques to ensure proper placement and device designs and techniques to remove devices which have been improperly placed.

Figure 2:
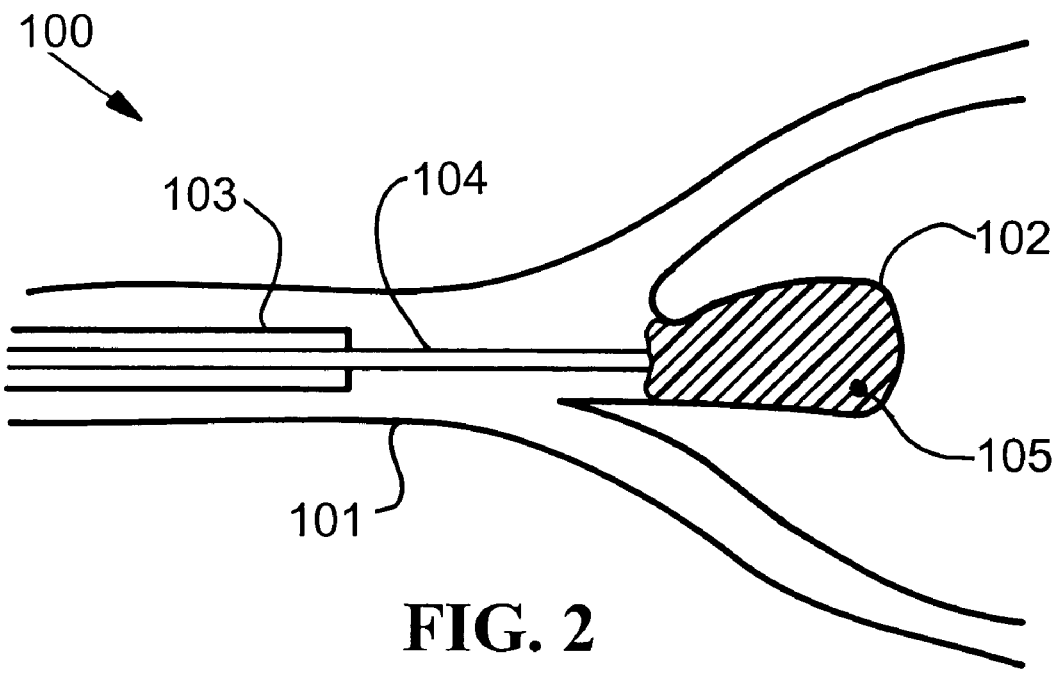
FIG. 2 is another view of the embodiment of the present invention shown in FIG. 1.

Referring now to FIGS. 1 and 2, two figures will be used to describe an embodiment of the present invention that provides a system for occluding a physical anomaly. The embodiment is designated generally by the reference numeral 100. FIGS. 1 and 2 are schematic illustrations of the working end of a system 100 for treating an arteriovenous malformation or aneurysm 102.

As shown in FIG. 1, a collapsed SMP foam device 105 is connected at the end of a guide wire 104. The SMP foam device 105 is placed inside the aneurysm 102. This is accomplished by delivering the SMP foam device 105 through a catheter 103 using the guide wire 104. The catheter 103 is inserted through the artery 101 to position the SMP foam device 105 in the aneurysm 102.

Referring now to FIG. 2 the SMP foam device 105 is shown actuated, thereby expanding it inside the aneurysm 102 and occluding the aneurysm 102. The SMP foam device 105 is expandable from 100% to 10000% in volume. The SMP foam device 105 is actuated by one of several means including electromagnetic energy delivered optically. The SMP foam device 105 is used to occlude part or all of a lumen, aneurysm, or artiovascular malformation. The expanded SMP foam device 105 is releasing from the end of the guide wire 104. The guide wire 104 is then retracted through the catheter 103. The catheter 103 is then retracted from the artery 101.

The SMP foam device 105 is made out of "shape memory polymer" (SMP). The SMP is a material which can be formed into a specific "primary" shape, reformed into a "secondary" stable shape, then controllably actuated so that it recovers its primary shape. The SMP device 105 has the structure of an open cell foam with porosity, pore size, and size distributions designed for each individual application.

The general concept behind the SMP foam device for aneurism therapy will be summarized with reference to FIGS. 1 and 2. The device consists of an SMP foam actuator 105 on the distal end, which is connected to the distal end of a catheter 103 or alternatively the distal end of a guide-wire assembly 104. The catheter 103 or guide wire 104 contains an optic fiber or alternative means to heat or radiate the SMP 105 for actuation. There is a coupling between the SMP foam 105 and the guide wire 103 which can be selectively disengaged. The SMP foam device 105 is made of a suitable biocompatible SMP, is loaded with a radiopaque additive, contains a laser dye suitable for vascular use, and is coated with a thrombogenic material such that upon actuation the large surface of the foam promotes rapid thrombus formation within the geometry of the foam and adhesion of the foam to the aneurysm wall. The foam device 105 can be made in a number of standard geometries for aneurysm, AVM, or vascular anomalies. For each use, a pre-made foam geometry is chosen which best fits the therapeutic need.

The present invention has uses wherever it is desirable to occlude a physical anomaly. For example, the present invention has use for the closure of an aneurysm for the prevention and/or treatment of a stroke.

Stroke is a major cause of mortality and the primary cause of long-term disability in the United States. Each year there are an estimated 700,000 occurrences of stroke, from which 150,000 people die and 400,000 are left with a significant deficit. The costs of caring for victims of stroke in the acute phase, for chronic care, and lost productivity amount to an estimated $40 billion per year. Approximately 20% of strokes are hemorrhagic and result from the rupture of either arteriovenous malformations (AVMs) or aneurysms. For aneurysm/AVM rupture, the incidence of death is about 29%, and an additional 20 to 30% of patients suffer neurologic deficits. Since an estimated 4% of aneurysm/AVMs rupture each year, a significant number of people (up to 3.5 million) have aneurysm/AVMs for years prior to stroke occurrence, indicating significant benefit from early preventative treatment.

There are three treatment modalities for neurovascular aneurysm/AVMs; namely, standard microsurgery, the introduction of agents which occlude parts or all of the aneurysm/AVM, and radio surgery. At present, the highest success rates are achieved using standard microsurgery in which the aneurysm/AVM is removed. However, microsurgery involves a great deal of trauma (cutting a hole in the skull), long recovery times, and can't be used for a significant minority of aneurysm/AVMs due to insufficient access or patient refusal. Radiosurgery involves applying a focused beam of radiation to vessel walls, resulting in shrinkage of the aneurysm/AVM. Radiosurgery is limited though to use in aneurysm/AVMs which are relatively small in size and carries with it the risk of damage to surrounding brain tissue.

An emerging modality is the endovascular introduction of occluding glues or metal coils for aneurysm/AVM stabilization and to promote healing. However, endovascular therapy based on current devices and materials results in cure rates of only 5-10% and carries a 3-5% risk of serious complications; these include adhesion of the catheter to the aneurysm/AVM, glue or solvent toxicity, escape of material creating embolic events downstream from the aneurysm/AVM, and aneurysm/AVM rupture.

The current FDA-approved endovascular procedure for treating aneurysms is the GDC (Guglielmi Detachable. Coil-Target Therapeutics, Fremont, Calif.). The embolic coils are delivered through an interventional guide catheter into the aneurysm. The guide catheter generally enters through the femoral artery and is then negotiated through the cardiovasculature into the cerebrovasculature. A typical guide catheter is the Tracker 18 from Target Therapeutics with a 0.018 inch (approximately 450 µm) working channel for delivering therapeutic devices. The tip of the guide catheter is placed in the aneurysm through the neck of the aneurysm using fluoroscopic (x-ray) image guidance. Successive coils are deposited such that they fill the volume of the aneurysm, resulting in reduced/eliminated blood flow in the aneurysm and, in turn, a greatly reduced risk of acute stroke. Once the blood flow in the aneurysm has been stopped, the body generally seals off the aneurysm resulting in complete patient recovery with no risk of hemorrhagic stroke. Therapy utilizing the GDC has a number of limitations including a long procedure time required to place several coils, the large mismatch between the mechanical properties of the coil and the vascular wall, and the possibility of a coil escaping from the aneurysm/AVM and lodging downstream, causing an embolic event.

SMP actuators are made of any polymeric material that exhibits a shape-memory effect and is suitable for use in this application. This includes:

Thermoplastic SMPs—thermoplastic polymers are those which can be heated into a melt state in which all prior solid shape memory has been lost, processed into a shape, and solidified. If need be they can be re-heated to their melt state and re-processed a number of times. In thermoplastic SMPs, the shape memory effect generally relates to the material having a multiphase structure in which the different phases have different thermal transitions, which may be due to glass transitions, crystalline melting points, liquid crystal-solid transitions, ionomeric transitions, etc. The primary shape is obtained by processing in the melt state above the highest transition temperature and then cooling to a temperature in which either a hard phase or other physical crosslink is formed to lock in that shape. The secondary shape is obtained by bringing the material to a temperature above its actuation temperature but below its melting temperature, mechanically shaping the material into its secondary shape, then cooling it below its actuation temperature. Suitable thermoplastic SMPs include block copolymers (linear di, tri, and multi-blocks; alternating; graft), immiscible polymer blends (neat and with coupling agents such as di or tri-block copolymers), semi-crystalline polymers, and linear polymers with ionomeric groups along the chain or grafted to the chain.

Thermosetting SMPs—thermosetting polymers are those which are processed into a part and simultaneously chemically crosslinked, so that the part is essentially one macromolecule. They cannot be re-processed by melting. In thermosetting SMPs the primary shape is obtained during the initial processing step involving crosslinking. The secondary shape is obtained by mechanically reshaping the material at a temperature or condition in which the material is in an elastomeric state. This secondary shape is locked in by cooling the material below the actuation temperature, which relates to a transition as described above. Suitable thermosetting SMPs include all of the types of materials described under thermoplastic SMPs but which can also be chemically crosslinked to form the primary shape. In addition, crosslinked homopolymers can also be used as SMPs with the actuation temperature typically being the glass transition temperature of the material.

Coil-rod transition SMPs are also used for the shape memory material actuator. Some polymers undergo a coil to rod transition in their chain conformation by relatively small changes in their environment, such as solvent changes or changes in the ionic character in an aqueous environment. Similarly, adsorption of electromagnetic radiation of a specific wavelength can cause changes in the conformation of certain polymers, which induces a macroscopic shape response. Both thermoplastic and thermosetting polymers which undergo such rod-coil transitions can be used for this application.

While all shape memory polymer compositions are suitable for the current invention, the compositions having the following properties are particularly suitable: (1) Transparency—this usually is a characteristic of an SMP which is two phase but with microphase sizes below about 50 microns, an SMP which is single phase and whose primary shape is fixed by covalent or ionic crosslinking, or a multiphase system in which all phases have very similar refractive indices. (2) The lowest transition temperature, used for actuation, is in the range of 20 C to 80 C. (3) The polymer is biocompatible (does not invoke immune response) and biodegradable over a controlled period of time. Biodegradation products should likewise be non-toxic. (4) SMPs which have hysteresis in the modulus temperature curve. This means that the thermal transition from the glassy to the rubbery state in the SMP is higher during heating than it is during cooling, such that following in-vivo actuation the SMP remains in an elastomeric state. The amount of the hysteresis, determined by the shift in the transition temperature as measured by DSC, would be in the range of 5 to 50° C. This shift could be due to melting of crystallinity responsible for the transition, absorption of physiological compounds which act as plasticizers, thermally induced mixing or demixing of the SMP itself, or chemical changes induced during actuation which change the Tg of the material. This property of the SMP would be important for preventing damage to tissue and organs during use. (5) The SMP can be blended with a radiogical contrast agent such as barium sulfate, tantalum oxide, etc. (6) The SMP can be made into a foam by traditional or porogen templating techniques. (7) The surface of the SMP device can be chemically functionalized or alternatively coated to promote the formation of a thrombus within the polymer structure. (8) The SMP can contain a dye suitable for adsorption of electromagnetic radiation with wavelengths in the range of 300 to 1200 nanometers. Dyes with adsorption peaks centered near 800 nm would be particularly suitable.

The SMP is ideally made into an open cell foam structure with a distribution of pore sizes in the range going from tens of nanometers to ca. 500 microns on the high end. The mean pore size should be in the range of 10 to 50 microns. Such a pore size and size distribution would be optimal for a therapeutic device used to treat aneurysm in the following regards: it would promote the rapid aspiration of blood into the device during expansion, including all components necessary for thrombus formation; it would allow for the making of foam structures with high expansibility (low density); pore size and distribution can be used also to help control the recovery forces imposed by the device on the aneurysm wall during expansion. The expansibility (Final volume/initial volume) of the foams claimed here are in the range of 200 to 20000%, or expansion ratios of 2 to 200.

Figure 3:
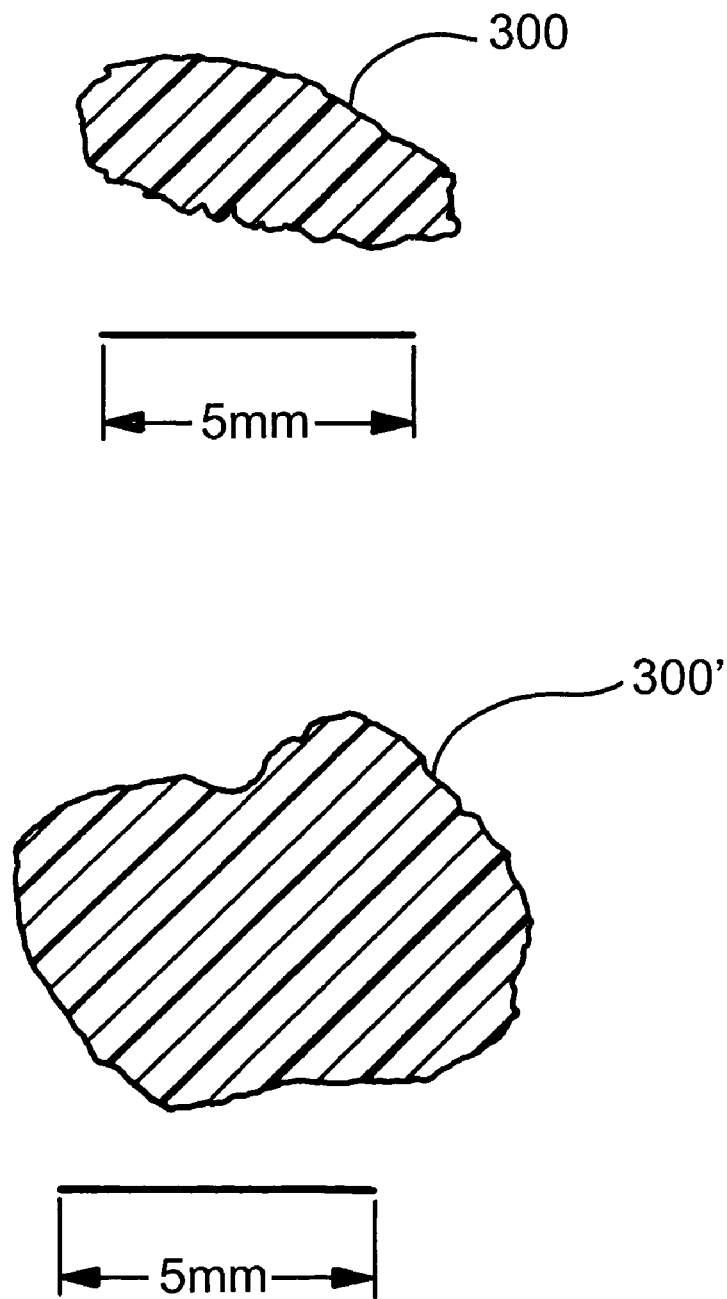
FIG. 3 illustrates an an example of SMP foam actuator.

Referring now to FIG. 3, an example of SMP foam actuator is illustrated. The SMP foam actuator designated by the reference numeral 300 is shown after being heated to 70 C, compressed, and cooled to room temperature under compression. The same SMP foam actuator designated by the reference numeral 300' is shown after 5 seconds at 70 C followed by cooling to room temperature. The SMP foam actuator 300/300' is an open cell foam composed of a polyurethane SMP. The foam is made using a 10% solution of SMP in DMSO impregnated into a pressed cube of sucrose crystals, followed by solvent removal, extraction of the sucrose with water, then dried. The SMP foam actuator can be made by a variety of techniques including: (1) Porogen templating, (2) Chemical blowing, (3) Solvent (physical) blowing, (4) Gas blowing, (5) Freeze drying SMP solutions, (6) High inverse phase emulsion process, or any combination of the above techniques.

The SMP actuator can be expanded by various mechanisms for actuation based on movement through a thermal transition. The mechanisms include optical heating, convective heating using a heat transfer medium, electrical resistance heating, inductive heating, x-ray induced reaction, and by exposure to biologically compatible solvents which can induce a change in the SMP thermal transitions when absorbed.

Figure 4:
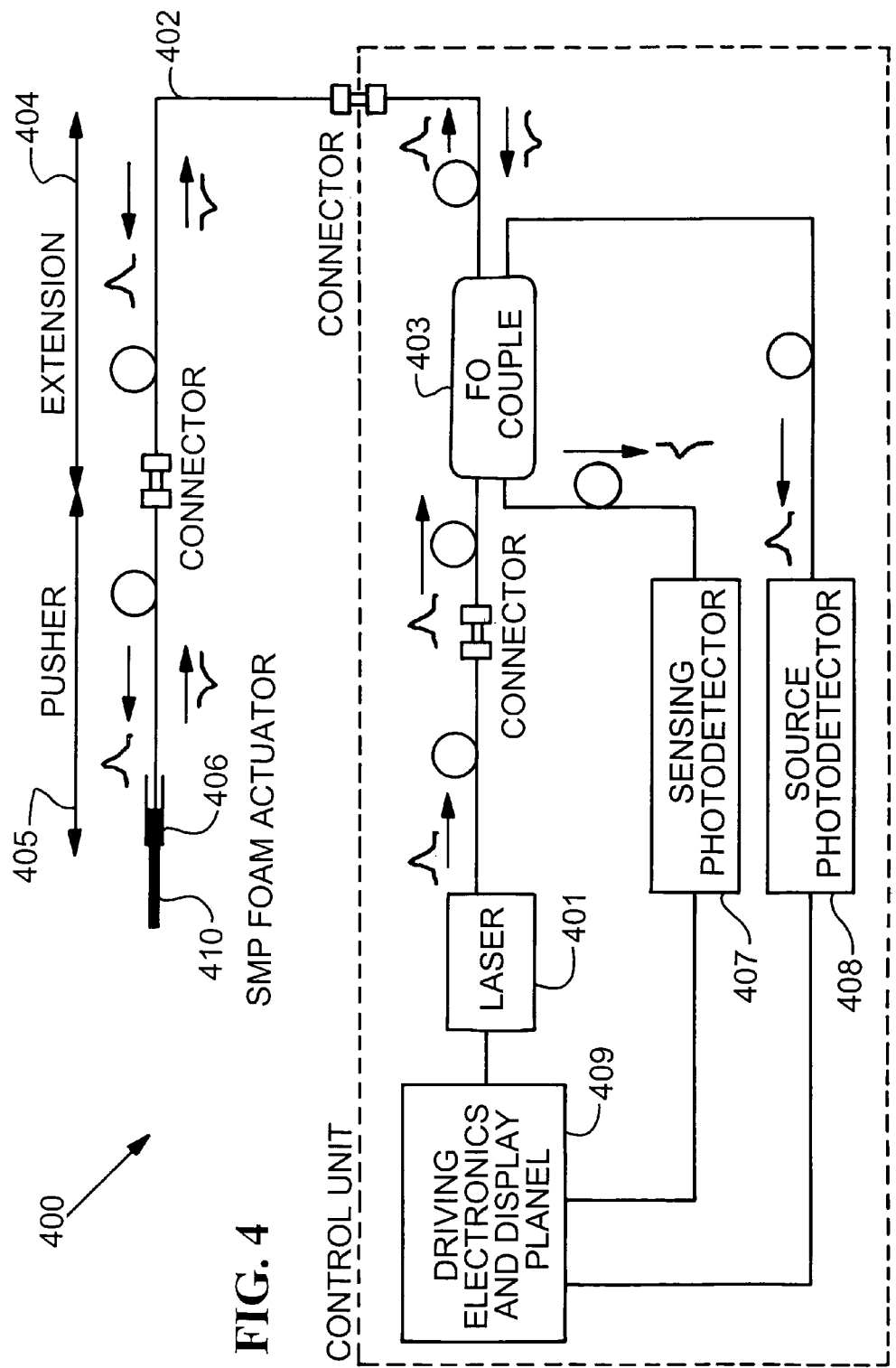
FIG. 4 illustrates a system for optical heating using optic fibers to transport light energy to the SMP actuator.

Referring now to FIG. 4, a system for optical heating using optic fibers to transport light energy to the SMP actuator as shown schematically. The system is designated generally by the reference numeral 400. FIG. 4 is a schematic overview of an ischemic stroke treatment system 400. Laser light from laser 401 is transmitted through a multimode optical fiber 402, a fiber coupler 403, an extension fiber 404 that enters the sterile surgical field, and a fiber pusher 405 with the SMP actuator 406 at the distal tip of the central tube and inner catheter 410. Separate fibers are used to actuate the central tube tip and the inner catheter tip for independent control. A small amount of laser light is reflected from the fiber-coil interface back through the coupler 403 into the photodetector 407. Source fluctuations may be monitored by the source photodetector 408. As the laser light heats the SMP 406 in the distal tip of the catheter, the umbrella deploys. As an optional design feature, detection of the actuation can be fed back to the operator (or computer) 409. The SMP 406 movement causes the reflected signal to decrease. The changes in the reflected signal can be used to control the driving current of the laser 401 or to alert an operator of the status of the actuator 406 (e.g., open or closed). The light can be absorbed by a suitable dye, which is incorporated into the SMP actuator uniformly, or in a gradient engineered to provide for even heating throughout the actuator geometry.

Optical heating may also be accomplished by placing the light absorbing dye in an elastomeric coating on the surfaces of the SMP actuator or in an aqueous media which is in contact with the SMP device. Optical heating is preferable from the standpoint that most of the energy applied is used to heat the SMP, minimizing thermal damage to the blood or tissue.

Convective heating may also be used for actuation of the SMP end by pumping a heated saline solution through the interstitial space between the inside of the guide catheter and the outside of the second catheter with the SMP actuator end. This approach can be combined with fiber-optic heating to boost the temperature of the saline to a needed level should cooling during transport through the catheter be a problem.

Inductive heating can be accomplished by filling the SMP with microparticles or nanoparticles of a material which can selectively absorb RF radiation, converting it to heat. By having an even distribution of particles in the SMP actuator and applying a uniform field the SMP can be quickly and evenly heated for actuation.

An SMP foam occlusion device as described above has the properties of being capable of catheter delivery, be easily and accurately positioned, have rapid and controlled expansion from a small initial size to a size and shape approximately that of the aneurysm or arteriovenous malformation (AVM) being stabilized, be made of biocompatible materials, stimulate the bodies own repair mechanisms for the aneurysm or AVM, and disappear without causing further injury as the vascular lumen repairs itself. The high expansibility of the device allows for treatment with a single or relatively small number of devices versus the current need for many (tens) coil type devices. While the SMP foam has fairly low modulus, the strength of the foam is sufficient to prevent it from being removed from the aneurysm due to blood flow in the adjoining lumen. The system of the present invention also allows for the removal of the SMP foam device via the delivery catheter should there be a problem with placement.

Referring now to FIGS. 5, 6, 7, and 8, different foam device systems are illustrated. The systems are designated generally by the reference numerals 500, 600, 700, and 800 in the four figures. In FIGS. 5 and 6 the SMP foam systems 500 and 600 are used to occlude and prevent further expansion of aneurysm 501. In FIG. 7 the SMP foam system 700 is used to occlude and prevent further expansion of arteriovenous malformation 701. In FIG. 8 the SMP foam system 800 is used to occlude and prevent further expansion of an enlarged capillary 801 shunting blood flow between arteries and veins.

The therapeutic devices 500, 600, 700, and 800 are delivered endovascularly via catheter. The primary method for placement of the devices 500, 600, 700, and 800 is via radiology. The devices 500, 600, 700, and 800 have sufficient radio-contrast through the use of radiopaque fillers or due to other aspects of composition. Other tools for determining placement include fiber-optic based imaging technologies such as OCT, etc.

The SMP foam devices 500, 600, 700, and 800 are released from the catheter or guide wire either during actuation due to expansion away from an interlocking geometry or following expansion through a second actuation event. The foam is mechanically attached to the guide wire or catheter and upon expansion, is released from the mechanical interlock. The collapsed device is shown in the expanded foam and various geometries that may be useful for the mechanical interlock. Other types of release mechanisms can be used for the SMP foam device based on the change in geometry of SMP and SMA devices on the catheter tip, to dissolution of a bonding material, to galvanic erosion of a connector, etc.

Once the SMP foam device has been placed, it is important that is stays in position and does not get pushed out into the channel with the desired blood flow pattern. There are a number of ways that the devices 500, 600, 700, and 800 can be held in place. First, the device can hold itself in place when it is situated in an aneurysm in which the aneurysm cavity is larger than the aneurysm opening. Upon thrombosis within the foam, it will be very difficult for the foam device to be pushed out. A second method for holding the device into that cavity is through the action of a diaphragm or other geometry which covers the aneurysm opening. In the case of the occlusion of a vascular shunt, the foam geometry is made longer and tends to hold it in place both by the tapered geometry of the vascular lumen and the hydrostatic pressure of the blood flow. Thrombosis of the blood within the foam will also help to hold it in place. A secondary device such as an SMP stent or coil structure can also be used to provide additional support.

Referring now to FIG. 9, a collapsed device 900 is shown. The collapsed SMP foam device 900 may be connected at the end of a guide wire or other system for delivery. The SMP foam device 900 is placed in the desired location. For example, this is accomplished by delivering the SMP foam device 900 through a catheter using a guide wire.

Referring now to FIG. 10, an expanded foam (actuated) device 100 is shown. For example the device 1000 can be expanding it inside the aneurysm and occlude the aneurysm. The SMP foam device 1000 is expandable from 100% to 10000%. The SMP foam device 1000 is actuated by one of several means including electromagnetic energy delivered optically. The SMP foam device 1000 can be used to occlude part or all of a lumen, aneurysm, or artiovascular malformation. The expanded SMP foam device 1000 can be releasing from the end of a guide wire. The guide wire can then retracted through the catheter. The catheter can then be retracted from the artery.

Referring now to FIG. 11, examples of guidewires having various geometries 1101, 1102, 1103, and 1104 are shown that may be useful for the mechanical interlock connecting the SMP foam to the end of a guide wire. The guidewire 1101 has a reduced diameter section near its distal end. The guidewire 1102 has a conical reduced diameter section near its distal end. The guidewire 1103 has a spherical expanded diameter section near its distal end. The guidewire 1104 has a reduced diameter section and an expanded diameter section near its distal end.

Figure 12:
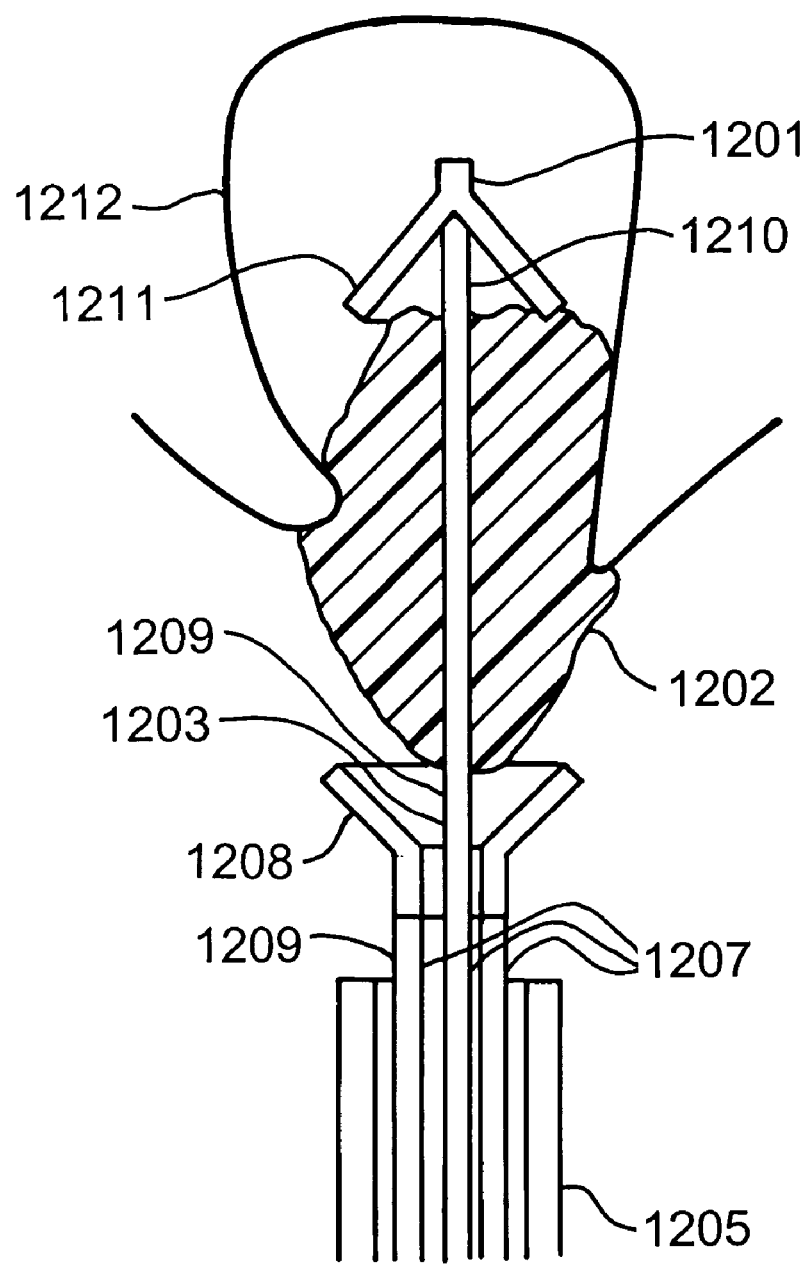
FIG. 12 illustrates another embodiment of the present invention.

Referring now to FIG. 12, another embodiment of the present invention is shown for retrieving a misplaced foam device. This embodiment is designated generally by the reference numeral 1200. The guidewire 1209 that is normally used for delivering a SMP foam device includes a second SMP (or other type) device 1201. The second SMP device 1201 can be separately expanded.

The various components of the system 1200 include a delivery catheter 1205, an inner catheter 1206 containing optical fibers 1207 and with a flaring SMP distal tip 1208, a guide wire 1209 with optic fiber 1210, and a SMP gripper/release device 1211. The misplaced SMP foam device 1202 is shown located in an aneurysm 1212. The secondary SMP device 1201 is at the distal end of the guidewire 1209 and can catch the misplaced foam 1202 and draw it back toward the catheter 1205. An alternate device would allow the SMP foam to be gripped on each side and stretched to form a thinner cylinder for withdrawal.

In operation, the guidewire 1209 is extended through the misplaced SMP foam. The second SMP device 1201 is expanded resulting in the misplaced foam 1202 being gripped between the distal end 1203 of the guidewire 1209 and the distal end of the second SMP expandable device 1201. The foam 1202 is then drawn back into the delivery catheter 1205 or simply removed by removable of the entire assembly while being gripped. The system 1200 facilitates withdrawal of a misplaced device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for endovascular therapy by occluding a physical anomaly, said anomaly having an interior, comprising:
a shape memory material body for positioning in the interior of the physical anomaly, wherein said shape memory material body comprises a shape memory polymer foam;
a delivery system for delivering said shape memory material body that comprises a shape memory polymer foam into the interior of the physical anomaly; and
a system for providing said shape memory material body that comprises a shape memory polymer foam with a primary shape for occluding the physical anomaly and a secondary shape for being delivered into the interior of the physical anomaly;
wherein said shape memory polymer foam is a shape memory polymer foam composed of a polyurethane shape memory polymer with an open cell foam structure.

2. The apparatus of claim 1 wherein said shape memory polymer foam is a shape memory polymer foam with an open cell foam structure including a light absorbing dye.

3. The apparatus of claim 1 wherein said system for providing said shape memory material body that comprises a shape memory polymer foam with a primary shape and a secondary shape comprises radiology.

4. The apparatus of claim 1 wherein said system for providing said shape memory material body that comprises a shape memory polymer foam with a primary shape and a secondary shape comprises electromagnetic energy.

5. The apparatus of claim 1 wherein said system for providing said shape memory material body that comprises a shape memory polymer foam with a primary shape and a secondary shape comprises electromagnetic energy delivered optically.

6. The apparatus of claim 1 wherein said shape memory material body that comprises a shape memory polymer foam is a collapsed shape memory polymer foam device connected at the end of a guide wire.

7. The apparatus of claim 1 wherein said system for providing said shape memory material body that comprises a shape memory polymer foam with a primary shape and a secondary shape comprises a system for optical heating using optic fibers to transport light energy to said shape memory material body that comprises a shape memory polymer foam.

8. The apparatus of claim 1 wherein said system for providing said shape memory material body that comprises a shape memory polymer foam with a primary shape and a secondary shape comprises a laser and an optical fiber wherein said laser transmits laser light through said optical fiber.

9. The apparatus of claim 1 wherein said system for providing said shape memory material body that comprises a shape memory polymer foam with a primary shape and a secondary shape comprises a laser and an optical fiber wherein said laser transmits laser light through a multimode optical fiber.

10. The apparatus of claim 1 wherein said system for providing said shape memory material body that comprises a shape memory polymer foam with a primary shape and a secondary shape comprises a light absorbing material.

11. The apparatus of claim 1 wherein said system for providing said shape memory material body that comprises a shape memory polymer foam with a primary shape and a secondary shape comprises a light absorbing dye in an elastomeric coating on said shape memory material body that comprises a shape memory polymer foam.

12. An apparatus for endovascular therapy by occluding an aneurism having an interior, comprising:
a shape memory polymer material body for being positioned in the interior of the aneurism, wherein said shape memory polymer material body comprises a shape memory polymer foam;
a delivery system for delivering said shape memory polymer material body that comprises a shape memory polymer foam into the interior of the aneurism; and
an activation system for providing said shape memory polymer material body with a primary shape for occluding the aneurism and a secondary shape for being positioned in the interior of the aneurism;
wherein said shape memory polymer material body that comprises a shape memory polymer foam is a collapsed shape memory polymer foam device connected at the end of a guide wire.

13. The apparatus of claim 12 wherein said shape memory polymer material body that comprises a shape memory polymer foam is a shape memory polymer foam with an open cell foam structure including a light absorbing dye.

14. The apparatus of claim 12 wherein said activation system for providing said shape memory polymer material body with a primary shape and a secondary shape comprises radiology.

15. The apparatus of claim 12 wherein said activation system for providing said shape memory polymer material body with a primary shape and a secondary shape comprises electromagnetic energy.

16. The apparatus of claim 12 wherein said activation system for providing said shape memory material body with a primary shape and a secondary shape comprises electromagnetic energy delivered optically.

17. The apparatus of claim 12 wherein said activation system for providing said shape memory polymer material body that comprises a shape memory polymer foam with a primary shape and a secondary shape comprises a system for optical heating using optic fibers to transport light energy to said shape memory polymer material body that comprises a shape memory polymer foam.

18. The apparatus of claim 12 wherein said activation system for providing said shape memory polymer material body that comprises a shape memory polymer foam with a primary shape and a secondary shape comprises a laser and an optical fiber wherein said laser transmits laser light through said optical fiber.

19. The apparatus of claim 12 wherein said activation system for providing said shape memory polymer material body that comprises a shape memory polymer foam with a primary shape and a secondary shape comprises a laser and an optical fiber wherein said laser transmits laser light through a multimode optical fiber.

20. The apparatus of claim 12 wherein said activation system for providing said shape memory polymer material body that comprises a shape memory polymer foam with a primary shape and a secondary shape comprises a light absorbing material.

21. The apparatus of claim 12 wherein said activation system for providing said shape memory polymer material body that comprises a shape memory polymer foam with a primary shape and a secondary shape comprises a light absorbing dye in an elastomeric coating on said shape memory polymer material body that comprises a shape memory polymer foam.

22. An apparatus for endovascular therapy by occluding a physical anomaly, said anomaly having an interior, comprising:
 a shape memory material body for positioning in the interior of the physical anomaly, wherein said shape memory material body comprises a shape memory polymer foam;
 a delivery system for delivering said shape memory material body that comprises a shape memory polymer foam into the interior of the physical anomaly; and
 a system for providing said shape memory material body that comprises a shape memory polymer foam with a primary shape for occluding the physical anomaly and a secondary shape for being delivered into the interior of the physical anomaly;
 wherein said system for providing said shape memory material body that comprises a shape memory polymer foam with a primary shape and a secondary shape comprises electromagnetic energy.

23. An apparatus for endovascular therapy by occluding a physical anomaly, said anomaly having an interior, comprising:
 a shape memory material body for positioning in the interior of the physical anomaly, wherein said shape memory material body comprises a shape memory polymer foam;
 a delivery system for delivering said shape memory material body that comprises a shape memory polymer foam into the interior of the physical anomaly; and
 a system for providing said shape memory material body that comprises a shape memory polymer foam with a primary shape for occluding the physical anomaly and a secondary shape for being delivered into the interior of the physical anomaly;
 wherein said shape memory material body that comprises a shape memory polymer foam is a collapsed shape memory polymer foam device connected at the end of a guide wire.

24. An apparatus for endovascular therapy by occluding an aneurism having an interior, comprising:
 shape memory polymer material body for being positioned in the interior of the aneurism, wherein said shape memory polymer material body comprises a shape memory polymer foam;
 a delivery system for delivering said shape memory polymer material body that comprises a shape memory polymer foam into the interior of the aneurism; and
 an activation system for providing said shape memory polymer material body with a primary shape for occluding the aneurism and a secondary shape for being positioned in the interior of the aneurism;
 wherein said activation system for providing said shape memory polymer material body with a primary shape and a secondary shape comprises electromagnetic energy.

* * * * *